US011779530B2

(12) United States Patent
Barhoum et al.

(10) Patent No.: US 11,779,530 B2
(45) Date of Patent: Oct. 10, 2023

(54) COMPOSITION FOR THE PERMANENT DEFORMATION OF HAIR HAVING REDUCED ODOR

(71) Applicant: Noxell Corporation, Hunt Valley, MD (US)

(72) Inventors: Moussa Barhoum, Frankfurt (DE); Manfred Schmitt, Bensheim (DE); Christine Marie Cahen, Bonn (DE); Graham Neil McKelvey, Schwalbach (DE)

(73) Assignee: WELLA OPERATIONS US, LLC, Calabasas, CA (US)

( * ) Notice: Subject to any disclaimer, the term of this patent is extended or adjusted under 35 U.S.C. 154(b) by 451 days.

(21) Appl. No.: 16/327,652

(22) PCT Filed: Sep. 14, 2017

(86) PCT No.: PCT/US2017/051642
§ 371 (c)(1),
(2) Date: Feb. 22, 2019

(87) PCT Pub. No.: WO2018/053183
PCT Pub. Date: Mar. 22, 2018

(65) Prior Publication Data
US 2019/0192408 A1   Jun. 27, 2019

(30) Foreign Application Priority Data
Sep. 14, 2016 (EP) ..................... 16188723

(51) Int. Cl.
| | |
|---|---|
| *A61K 8/49* | (2006.01) |
| *A61Q 5/04* | (2006.01) |
| *A61K 8/46* | (2006.01) |
| *A61K 8/19* | (2006.01) |
| *A45D 7/04* | (2006.01) |
| *A61K 8/37* | (2006.01) |
| *A61K 8/40* | (2006.01) |
| *A61K 8/44* | (2006.01) |
| *A61K 8/73* | (2006.01) |
| *A61K 8/81* | (2006.01) |
| *A61K 8/92* | (2006.01) |

(52) U.S. Cl.
CPC ............ *A61K 8/4973* (2013.01); *A45D 7/04* (2013.01); *A61K 8/19* (2013.01); *A61K 8/37* (2013.01); *A61K 8/40* (2013.01); *A61K 8/44* (2013.01); *A61K 8/46* (2013.01); *A61K 8/498* (2013.01); *A61K 8/731* (2013.01); *A61K 8/817* (2013.01); *A61K 8/922* (2013.01); *A61Q 5/04* (2013.01); *A61K 2800/87* (2013.01); *A61K 2800/882* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 3,099,603 A | 7/1963 | Banker et al. | |
| 5,294,230 A * | 3/1994 | Wu | A61Q 5/04 132/203 |
| 10,709,804 B2 * | 7/2020 | Tranzeat | A61Q 13/00 |
| 2003/0068295 A1 | 4/2003 | Rohde et al. | |
| 2006/0207037 A1 | 9/2006 | Fadel et al. | |
| 2007/0190007 A1 | 8/2007 | Savaides et al. | |
| 2012/0186597 A1 * | 7/2012 | Hawkins | A45D 7/00 132/206 |

FOREIGN PATENT DOCUMENTS

| | | |
|---|---|---|
| JP | 2014240360 A | 12/2014 |
| KR | 20000025753 A | 5/2000 |
| WO | WO-8802997 A1 | 5/1988 |
| WO | WO-2018053183 A1 | 3/2018 |

OTHER PUBLICATIONS https://www.epa.gov/chemical-research/distributed-structure-searchable-toxicity-dsstox-database (Year: 2004).*
https://pubchem.ncbi.nlm.nih.gov/source/hsdb/626.*
"European Application Serial No. 16188723.7, Office Action dated Jun. 9, 2020", 15 pgs.
"International Application Serial No. PCT/US2017/051642, International Preliminary Report on Patentability dated Mar. 28, 2019", 8 pgs.
"European Application Serial No. 16188723.7, Communication Pursuant to Article 94(3) EPC dated Nov. 16, 2018", 3 pgs.
"European Application Serial No. 16188723.7, Extended European Search Report dated Feb. 24, 2017", 7 pgs.
"European Application Serial No. 16188723.7, Response filed Jan. 16, 2019 to Communication Pursuant to Article 94(3) EPC dated Nov. 16, 2018", 92 pgs.
"European Application Serial No. 16188723.7, Response filed Aug. 29, 2018 to Extended European Search Report dated Feb. 24, 2017", w/ English Claims, 38 pgs.
"International Application Serial No. PCT/US2017/051642, International Search Report dated Oct. 30, 2017", 6 pgs.
"International Application Serial No. PCT/US2017/051642, Written Opinion dated Oct. 30, 2017", 8 pgs.

* cited by examiner

*Primary Examiner* — David J Blanchard
*Assistant Examiner* — Sarah J Chickos
(74) *Attorney, Agent, or Firm* — Dennemeyer & Associates LLC; Victoria Friedman

(57) ABSTRACT

The present invention relates to a permanent shaping composition for the permanent deformation of hair comprising, in a cosmetically acceptable carrier, at least one reducing agent comprising a mercapto functional group, at least one alkalizing agent, and a malodor suppressant system comprising at least a first malodor suppressant, herein the first malodor suppressant has a molecular weight of from 100 to 400 g/mol, and wherein the malodor suppressant system has a distribution coefficient log P (octanol/water) of 2 or more.

5 Claims, No Drawings

COMPOSITION FOR THE PERMANENT DEFORMATION OF HAIR HAVING REDUCED ODOR

PRIORITY

This application is a U.S. National Stage Filing under 35 U.S.C. 371 from International Application No. PCT/US2017/051642, filed on Sep. 14, 2017, and published as WO 2018/053183 on Mar. 22, 2018, which application claims the benefit of priority from EP Patent Application No. 16188723.7, filed on Sep. 14, 2016, which are herein incorporated in their entirety by reference.

FIELD OF INVENTION

The present invention relates to a permanent shaping composition for the permanent deformation of hair.

BACKGROUND OF THE INVENTION

The classic technique for permanent hair shaping, i.e., permanent waving and straightening of hair, is familiarly on two treatment steps: In the first step, the cystine-disulfide bridges of the keratin of the hair are opened by the action of a composition that comprises a reducing ingredient (permanent shaping composition). The hair is then put into the desires shape. In a second step, cystine-disulfide bonds are closed again using a fixative, that is, a composition comprising an oxidizing ingredient.

As classic reducing agents, compounds comprising mercapto-functional groups are used, for example thioglycolic acid, ammonium or monoethanolamine salts of thioglycolic acid, 2-mercaptopropionic acid (thiolactic acid), 3-mercaptopropionic acid, cysteine, and derivatives of these compounds, cysteamine, mercaptocarboxylic acid esters, and N-alkyl-2-mercaptoacetamides.

The first step, i.e., the cystine-disulfide opening reaction, is typically carried out at a pH of 7.5 to 9 in the presence of an alkalizing agent. The alkaline-adjusted permanent shaping compositions based on mercapto-functionalized reducing agents, however cause unpleasant odor. The unpleasant odor of the reducing agents requires intensive perfuming of the products.

Despite the fact that commercial permanent hair deformation products have been available for many years, still no products exist which effectively reduce or even completely avoid the malodor during and after the hair shaping process, and simultaneously provide an effective permanent hair shaping effect.

By using thiolactic acid, it is possible to slightly reduce the malodor. In comparison to the widely used thioglycolic acid, the permanent deformation effectiveness of thiolactic acid is however considerably weaker.

SUMMARY OF THE INVENTION

The present invention relates to a permanent shaping composition for the permanent deformation of hair comprising, in a cosmetically acceptable carrier, at least one reducing agent comprising a mercapto functional group, at least one alkalizing agent, and a malodor suppressant system comprising at least a first malodor suppressant, a second malodor suppressant, and, optionally, a second malodor suppressant and/or one or more further malodor suppressants, wherein the first malodor suppressant is different from the second malodor suppressant, and wherein each of the first and second malodor suppressants have a molecular weight of from 100 to 400 g/mol, and wherein the malodor suppressant system has a distribution coefficient log P (octanol/water) of 2 or more. The present invention further relates to a kit for the permanent deformation of hair comprising an individually packaged composition comprising at least one reducing agent comprising a mercapto functional group and at least one alkalizing agent, an individually packaged malodor suppressant system, and, optionally, an individually packaged fixing composition comprising an oxidizing agent. The present invention further relates to a method for the permanent deformation of hair comprising providing a permanent shaping composition by mixing at least one reducing agent comprising a mercapto functional group, at least one alkalizing agent and a malodor suppressant system, applying the permanent shaping composition to the hair, allowing the permanent shaping composition to act on the hair, rinsing the hair with water, applying to the hair a fixing composition comprising an oxidizing agent for performing an oxidative post-treatment of the hair, and rinsing the hair with water. The present invention further relates to a use of a malodor suppressant system in a composition for the treatment of hair, especially in a permanent shaping composition for the permanent deformation of hair.

It has now been found that a malodor suppressant system with specific features regarding its distribution coefficient and the molecular weight of the malodor suppressants comprised therein provides for a significantly reduced or even eliminated malodor in permanent hair shaping compositions.

In one aspect, the present invention relates to a permanent shaping composition for the permanent deformation of hair comprising, in a cosmetically acceptable carrier,
 (a) at least one reducing agent comprising a mercapto functional group,
 (b) at least one alkalizing agent, and
 (c) a malodor suppressant system comprising at least a first malodor suppressant,
wherein the first malodor suppressant has a molecular weight of from 100 to 400 g/mol, and wherein the malodor suppressant system has a distribution coefficient log P (octanol/water) of 2 or more.

In a further aspect, the invention relates to a kit for the permanent deformation of hair comprising
 A. an individually packaged composition comprising
  (a) at least one reducing agent comprising a mercapto functional group, and
  (b) at least one alkalizing agent;
 B. an individually packaged malodor suppressant system
  (c) comprising at least a first malodor suppressant, wherein the first malodor suppressant has a molecular weight of from 100 to 400 g/mol, and wherein the malodor suppressant system has a distribution coefficient log P (octanol/water) of 2 or more; and
 C. optionally, an individually packaged fixing composition comprising an oxidizing agent.

In a further aspect, the invention relates to a method for the permanent deformation of hair comprising the following steps:
 i. providing a permanent shaping composition by mixing
  (a) at least one reducing agent comprising a mercapto functional group,
  (b) at least one alkalizing agent, and
  (c) a malodor suppressant system comprising at least a first malodor suppressant wherein the first malodor suppressant has a molecular weight of from 100 to 400 g/mol, and wherein the malodor suppressant system has a distribution coefficient log P (octanol/water) of 2 or more;

ii. applying the permanent shaping composition to the hair before or after putting the hair in a desired shape;

iii. allowing the permanent shaping composition to act on the hair for a predetermined acting time sufficient for the permanent shaping of the hair;

iv. rinsing the hair with water;

v. applying to the hair a fixing composition comprising an oxidizing agent for performing an oxidative post-treatment of the hair; and vi. rinsing the hair with water.

In a further aspect, the invention relates to a use of a malodor suppressant system comprising a first malodor suppressant, a second malodor suppressant, and, optionally, one or more further malodor suppressants, wherein the first malodor suppressant is different from the second malodor suppressant, wherein each of the first and second malodor suppressants have a molecular weight of from 100 to 400 g/mol, and wherein the malodor suppressant system has a distribution coefficient log P (octanol/water) of 2 or more, in a composition for the treatment of hair, especially in a permanent shaping composition for the permanent deformation of hair.

DETAILED DESCRIPTION OF THE INVENTION

It is therefore a main objective of the present invention to provide a composition and a method for permanent shaping hair which significantly improves the odor during and after the shaping process of the hair, provides an effective permanent hair shaping performance, and which enhances the customer's acceptance of permanent hair shaping products.

A further objective of the present invention is to provide a permanent shaping composition and method that delivers unique elasticity and strength of the shaped hair from the tip to the root, an improved uniformity of the shaped hair with less disordered appearance.

A further objective of the present invention is to provide a composition and a method for permanent shaping hair which has superior hair care effects especially with regard to improved soft feel of wet and dry hair, improved elasticity of hair and durable waving of the hair.

Another objective of the present invention is to provide a composition and a method for permanent shaping hair which causes less hair damage than compositions of the prior art.

A further objective of the present invention is to provide a composition and a method for permanent shaping hair which penetrates well into the hair but less into the skin than compositions of the prior art.

As used herein the term "hair" may be "living", i.e., on a living body, or may be "non-living", i.e., in a wig, hairpiece or other aggregation of non-living keratinous fibers. Mammalian, preferably human hair is preferred. However wool, fur and other keratin containing fibers are suitable substrates for the compositions according to the present invention.

As used herein, the term "permanent shaping composition" relates to compositions used in the first step of the permanent deformation of hair, i.e., for the cystine-disulfide opening reaction. The permanent shaping composition is referred hereinafter as "the composition", unless otherwise specified. Permanent shaping compositions according to the invention may be used for both, permanent waving (i.e. curling of human hair) and straightening, (i.e. smoothing of human hair).

All percentages are by weight of the permanent shaping composition, i.e. of the ready-to-use composition which is the composition to be applied on hair, unless otherwise specified. When a ready-to-use composition is prepared by mixing two or more components comprising ingredients to be mixed for the desired effect, the amount of these ingredients is generally provided based on the weight of the component comprising such an ingredient, in case of the present text, e.g., the malodor system (c). Also ratios are weight ratios unless specifically stated otherwise.

The term "malodor suppressant system" means a mixture of two or more malodor suppressants.

The first aspect of the present invention is a permanent shaping composition for the permanent deformation of hair comprising, in a cosmetically acceptable carrier, (a) at least one reducing agent comprising a mercapto functional group, (b) at least one alkalizing agent, and (c) a malodor suppressant system comprising at least a first malodor suppressant, wherein the first malodor suppressant has a molecular weight of from 100 to 400 g/mol, and wherein the malodor suppressant system has a distribution coefficient log P (octanol/water) of 2 or more.

Cosmetically Acceptable Carrier

The composition comprises a cosmetically acceptable carrier or solvent. The solvent may be selected from water, or a mixture of water and at least one organic solvent to dissolve the compounds that would not typically be sufficiently soluble in water.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglycol, polyglycerol); propylene carbonate; and mixtures thereof.

The solvent may be selected from the group consisting of water, ethanol, propanol, isopropanol, glycerol, 1,2-propylene glycol, hexylene glycol, ethoxy diglycol, and mixtures thereof.

The composition may comprise water as a main ingredient, particularly in a total amount ranging from at least 50%, alternatively from at least 60%, alternatively from at least 70%, based on the total weight of the composition. Typically, when present, the composition comprises a total amount of organic solvents ranging from 1% to 30%, based on the total weight of the composition.

(a) Reducing Agent

The composition comprises at least one reducing agent. The reducing agent comprises a mercapto-functional group.

According to the present invention, generally all reducing agents known in the art which are suitable for use in the permanent deformation of hair can be used.

Suitable reducing agents are for example thioglycolic acid and thiolactic acid as well as the salts thereof, in particular the ammonium and ethanolamine salts. Further useful thio compounds are in particular cysteine or the hydrochloride thereof, homocysteine, cysteamine, N-acetyl cysteine, thioglycerol, ethanediol monothioglycolate, 1,2-propyleneglycol monothioglycolate, 1,3-propanediol monothioglycolate or the isomer mixture resulting therefrom, 1,3-butanediol and 1,4-butanediol monothioglycolate and the isomer mixtures therefrom, polyethylene glycol monothioglycolates, such as di-, tri- and tetraethyleneglycol monothioglycolates, glycerol monothiolactate, mercapto carboxylic acids and esters thereof, N-alkyl-2-mercaptoacetamides, as well as combinations of two or more thereof. The use of inorganic reducing sulfur compounds such as sodium hydrogen sulfite is basically also possible. Preferably, the reducing agent is selected from the group consisting of cycteine, thioglycolic acid, thiolactic acid, and salts thereof.

The permanent shaping compositions according to the present invention comprise at least one reducing compound at a concentration of at least 0.1 wt.-%, preferably at least 0.5 wt.-%, more preferably at least 1 wt.-%, based on the total weight of the composition. The total reduction agent content in the compositions according to the invention customarily amounts from 0.1 to 35 wt.-%, preferably from 0.5 to 20 wt.-%, more preferably 1 to 15 wt.-%, based on the total weight of the composition.

(b) Alkalizing Agent

The composition comprises at least one alkalizing agent. Alkalizing agents preferred within the scope of the invention are for example ammonia, ammonium carbamate, ammonia, ammonium(bi)carbonate, monoethanolamine, diethanolamine, triethanolamine, 2-amino-2-methyl-1-propanol, 2-amino-2-methyl-1,3-propanediol, 2-amino-2-ethyl-1,3-propanediol, 2-amino-1-butanole, tris(hydroxylmethyl)-aminomethane, tris-(2-hydroxypropyl)-amine, lysine, 2,2-iminobisethanol, iminourea (guanidine carbonate), tetrahydro-1,4-oxazine, 2-amino-5-guanidin valeric acid, 2-aminoethansulfonic acid, N-methyl ethanolamine, isopropanolamine, diisopropanolamine, triisopropanolamine, glucamine, sodium hydroxide, potassium hydroxide, lithium hydroxide, magnesium hydroxide, other water-soluble physiologically tolerable salts of organic and inorganic bases, and combinations of two or more thereof.

By varying the pH value, a composition can be made available that is universally suitable for every hair structure, optionally with the additional application of heat. The composition brings about an elastic, durable and uniform waving from the root of the hair to the ends, without eliciting allergic or sensitizing reactions. It is desirable to adjust the pH value to between about 5.5 and 12, preferably about 6.5 and 10.5, most preferably about 7.5 to 9.5. Thus, the quantity of the alkalizing agent is dependent on the reducing agent and the desired pH value of the composition.

The permanent shaping composition preferably comprises 0.1 to 10 wt.-%, more preferably 0.2 to 5 wt.-% of the alkalizing agent, based on the total weight of the composition.

(c) Malodor Suppressant System

The composition comprises a malodor suppressant system. The malodor suppressant system comprises at least a first malodor suppressant. The first malodor suppressant has a molecular weight of from 100 to 400 g/mol. The malodor suppressant system has a distribution coefficient log P (octanol/water) of 2 or more.

The malodor suppressant system may comprise only one first malodor suppressant. Such systems are one-component malodor suppressant systems ("one-component system") which do not comprise any further malodor suppressants having a log P (octanol/water) of 2 or more and a density of 1.1 g/mL or less, preferably no further suppressants selected from the group of compounds described below and named "list of malodor suppressants".

Preferably, the malodor suppressant system comprises at least a first malodor suppressant and at least a second malodor suppressant, i.e., a two-component malodor suppressant system ("two-component system"). Optionally, the malodor suppressant system may comprise one or more further malodor suppressants. The first and the second malodor suppressants are different. Each of the first and second malodor suppressants have a molecular weight of from 100 to 400 g/mol. The malodor suppressant system has a distribution coefficient log P (octanol/water) of 2 or more.

Unless otherwise indicated, the following description relating to the first malodor suppressant defines both, the first malodor suppressant in one-component systems and in two-component systems.

In the fields of organic and medicinal chemistry, a distribution (P) coefficient is the ratio of concentrations of a compound in the two phases of a mixture of two immiscible solvents at equilibrium. Hence these coefficients are a measure of differential solubility of the compound between these two solvents. One of the solvents chosen is water while the second is octanol. Hence the partition coefficient is a measure of how hydrophilic ("water loving") or hydrophobic ("water fearing") a chemical substance is. The partition coefficient is the ratio of concentrations of un-ionized compound between the two solutions. The logarithm of the ratio of the concentrations of the un-ionized solute in the solvents is called log P:

$$\log P_{oct/wat} = \log\left(\frac{[solute]_{octanol}^{un\text{-}ionized}}{[solute]_{water}^{un\text{-}ionized}}\right).$$

The log P (octanol/water) is referred hereinafter as "log P", unless otherwise specified.

It can be preferred that the malodor suppressants comprise at least one functional group selected from the group consisting of keto groups, aldehyde groups, ether groups, ester groups and hydroxyl groups. The first and the second malodor suppressants can comprise or two or more of such groups, either of the same type or of one or more different types.

The first malodor suppressant has a log P (octanol/water) of at least 2, preferably of at least 3. Preferably, the first malodor suppressant has a log P (octanol/water) of less than 9. More preferably, the first malodor suppressant has a log P (octanol/water) in the range of from 2 to less than 9, for example in the range of from 3 to less than 9.

The first second malodor suppressant has a log P (octanol/water) of at least 2, preferably of at least 3. Preferably, the second malodor suppressant has a log P (octanol/water) of less than 9. More preferably, the second malodor suppressant has a log P (octanol/water) in the range of from 2 to less than 9, most preferably in the range of from 3 to less than 9.

While generally all types and combinations of malodor suppressants according to the teaching of the present invention provide for a reduced malodor of the compositions, it has proven to be advantageous in many cases if at least the first malodor suppressant has a log P (octanol/water) of less than 9. In a further embodiment of the invention at least the first and the second malodor suppressant have a log P (octanol/water) of less than 9.

The first and second malodor suppressants may be a liquid at 23° C. and 1013 mbar. Preferably, the malodor system (c) is a liquid at 23° C. and 1013 mbar. It may also be preferred that the first and second malodor suppressants form a solution upon mixing.

It may also be preferred that at least two malodor suppressants in a combination of first and second malodor suppressants have a log P (octanol/water) of 3 or more and a molecular weight in the range of from 100 to 400 g/mol.

It is also possible that the malodor suppressant system comprises a first malodor suppressant being a compound having a distribution coefficient log P (octanol/water) of 2 or more and a molecular weight of between 100 and 400 g/mol and at least a second malodor suppressant being a compound having a distribution coefficient log P (octanol/water) of 3 or more and a molecular weight of between 100 and 400 g/mol, the first malodor suppressant and the second malodor suppressant being different compounds and at least one of the first and second malodor suppressants being liquid at 23° C. and 1013 mbar and the first and second malodor suppressant forming a solution upon mixing.

It has further been found that a permanent shaping composition according to the invention has especially good malodor suppression properties, if the density of the malodor suppressant system (c) present in the permanent shaping composition divided by the density of the permanent shaping composition without the malodor suppressant system (c) is 1.1 or less.

The density ratio mentioned above is thus measured for the malodor suppressant system (c), and is advantageously about 1.1 or less, and should advantageously be higher than about 0.85. Preferably, the density ratio ranges from about 1.09 to about 0.87, or from about 1.05 to about 0.88, or from about 1.01 to about 0.9, or from about 1.0 to about 0.92.

The density of the malodor suppressant system (c) is preferably about 1.1 g/mL or less, and should advantageously be higher than about 0.85 g/mL. Preferably, the density of the malodor suppressant system (c) ranges from about 1.09 to about 0.87 g/mL, or from about 1.05 to about 0.88 g/mL, or from about 1.01 to about 0.9 g/mL, or from about 1.0 to about 0.92 g/mL.

The density of at least one of the malodor suppressants is preferably about 1.1 g/mL or less, and should advantageously be higher than about 0.85 g/mL. Preferably, the density of at least one of the malodor suppressants ranges from about 1.09 to about 0.87 g/mL, or from about 1.05 to about 0.88 g/mL, or from about 1.01 to about 0.9 g/mL, or from about 1.0 to about 0.92 g/mL. More preferably, the density of each of the malodor suppressants is preferably about 1.1 g/mL or less, and should advantageously be higher than about 0.85 g/mL. Preferably, the density of each of the malodor suppressants ranges from about 1.09 to about 0.87 g/mL, or from about 1.05 to about 0.88 g/mL, or from about 1.01 to about 0.9 g/mL, or from about 1.0 to about 0.92 g/mL.

All densities relate to a temperature of 23° C. and a pressure of 1.013 bar. Density measurements are typically performed via determining the weight and the volume of the compound to be measured, or according to any other processes known to the skilled person.

Generally, it has proven to be successful for the one-component system if the first malodor suppressant is selected from the group consisting of Galaxolide, Operanide, Okoumal, habanolide and isopropylmyrstate.

Generally, it has proven to be successful for the two-component system if the first and second malodor suppressants are selected from the group consisting of (hereinafter called "list of malodor suppressants"): isopropylmyristate, galaxolide, habanolide, Operanide, Okoumal, Silkolide, Musk Plus, Helvetolide, Romandolide, Celestolide, Scentenal, hydroxycitronellal, o-Cresol, Para Cresol, linalool oxide (furanoid), Coumarone, methyl benzoate, Canthoxal, Cyclopidene, Methyl Octalactone, iso-butyvan, ethyl valerate, natural (US), hexyl aldehyde, benzyl methyl ether, Isopimpinellin, hydroxyol, trifernal, p-Tolyl acetate, allyl phenoxy acetate, methyl anthranilate, Eugewhite, 4.phenyl-2-butanol, Dihydroisophorone, Gardamide, 3-hexenyl acetate, cis-3-hexenyl acetate, cyclohexyl ethyl alcohol, phenoxyl ethyl propionate, 5-methyl-3-heptanone, 3-heptanol, 4-vinylphenol, methyl amyl ketone, iso-propyl 2-methylbutyrate, methyl heptenone, 4-ethylguaiacol, Ultravanil, furfuryl methyl sulfide, methyl laitone, methoxy melonal, dimethyl benzyl carbinol, 2-isopropyl-N-2,3-trimethylbutyramide, benzyl methoxyethyl acetal, Methoxy-isobutylpyrazine, 2-isopropyl-4-methyl thiaole, Benzoin, koumalactone, pyranol, Indoflor Crist., florex, trans-cinnamic acid, cinnamyl formate, keone, 8-bydroxy-para-cymene, linalool oxide, spirodecane, phenyl ethyl acetate, 2-isobutylthiazole, 2,4-dimethyl phenol, ethyl tiglate, Ethyl Phenyl Acetate, buccoxime, Verbenone, methyl phenyl carbonyl acetate, cinnamalva, cinnamyl nitrile, oxane, 4-isopropylbenzyl alcohol, benzyl propionate, 2-heptanol, methyl cinnamate, ethyl methyl phenyl glycidate, p-tolylacetate, heliotropin diethyl acetal, p-butyrylphenol, amyl vinyl carbinol, agarbois, muguesia, synthetic methyl salicylate, D-dihydrocarvone (mixture of isomers), d-p-8(9)-menthen-2-one, trans-dihydrocarvone, indol, benzyl ethyl ether, nonalactone, cis-limonene oxide, methyl jasmonate, ethyl-2-methyl pentanoate, pentanoic acid, 2-methyl-ethyl ester (S)-2,cis-Tagetone, eugenol, hexyl formate, nerolione, montaverdi, camphor gum, (5E)-2,6-Dimethyl-1,5,7-octatrien-3-ol, thujone, ethyl amyl ketone, Longozal, ionone epoxide beta, methyl hexyl ketone, methyl lavender ketone, 2,10-epoxypinane, amyl acetate and isomer blends, butyl butyrate, cis-6-nonen-1-ol FCC, (E,Z)-3,6-nonadien-1-ol, 3,6-nonadien-1-ol, 3,6-nonadien-1-ol, phenoxy ethyl iso-butyrate, 2,6-Nonadien-1-ol, cis-3-heptenyl acetate, cis-3-hexenyl pripionate, heptanal, ocimenol, iso-eugenol acetate, (E)-isoeugenol, cis-iso-eugenol, iso-eugenol, myrtenal, dimethyl anthranilate, 3-propylidenephthalide, 4-methyl quinoline, para-methyl quinoline, allyl amyl glycolate, cinnamyl acetate, cis-sabinol, D,L-borneol, iso-borneol, perilla aldehyde, skatole, 4-ethylphenol, p-ethyl phenol, Eugenyl Acetate, Hydratropic Aldehyde Dimethyl Acetal, 2,6-Nonadien-1-al, E Z-2,6-Nonadien-1-al, e,e,-2,6-nonadien-1-al, Myristicin, Leaf acetal, Leguminal, Azurone, alpha-Fenchyl Alcohol, fructalate, dihydro-eugenol, trans,trans-2,4-Nonadienal, L-Fenchone, fenchone, 3,5,5-Trimethyl-1-hexanol, dihydrotagetone, 3-Methyl-4-phenylpyrazole, Aladinate, Cyclohexyl acetate, plicatone, 1-Oxaspiro[5.5]undecan-4-ol, 4-methyl-, Myroxide, 1-phenyl-2-thujanol, 4-thujanol, Heptyl alcohol, Heptyl alcohol, Livescone, decahydro-2-nphtol, Asarone, phenyl ethyl dimethyl carbinol, methyl-iso-eugenol, p-cresyl methyl ether, Isoamyl isobutyrate, myrcenol super, gamma-decalactone, safrole, diethylphthalate, delta-decalactone, Methyl Eugenol, Para Cresyl iso-Butyrate, cis-jasmone, 2-phenyl-3-(2-furyl)prop-2-enal, Phenethyl propionate, Melozone, Octanol-3, indocolore, Methoxycitronellal PG, Rhodinol 70, Jasmacyclene, violiff, 4-pentenophenone, d-carvone (synthetic) FCC, L-carvone, L-carvone, benzyl butyrate, ringonol50 tec, propenyl guathol, 3-Cyclohexene-1-methanol, 3,5-dimethyl-, Clarycet, delphone, iso-cyclocitral, beta-Terpineol, hexyl acetate, Benzyl Iso Butyrate, styrallyl propionate, Amyl Propionate, amyl propionate, ethyl caproate FCC, Ethyl Hexyl Ketone, dehydroxy linalool oxide, triplal extra, ethyl cinnamate, cumin acetaldehyde, Plinol, Lyral, eucalyptol, Anapear, 1-ethyl-3-methoxytricycloheptane, Cyclohexylmagnol, Dipropyl sulphide, methyl dihydro jasmonate, trans-Hedione, 3,5,5-Trimethylhexanal, iso-pentyrate, cyclo-galbanate, butyl butyryl lactate FCC, cis-Carveol, 1-Carveol, (±)-Dihydrocarveol, dihydrocarveol, Iso Pulegol, dihydro-iso-jasmonate, LRG, Herboxane, 3,5,5-trimethylcyclohexanol, isoamly butyrate, Efetaal, Cantryl, zenolide, Isononanol, dimetol, verdural B extra, benzophenone, phenyl hexanol, caprylic acid (natural), Isobutyl angelate, rosaphen, Dimethyl Octenone, ligustral or triplal, para-menth-3-en-1-ol, dihydroterpineol, patchon, trans-2-tert-Butylcyclohexanol, verdol, 2(10)-pinen-3-ol, Fruitnat, octyl alcohol, Magnolan, ethyl salicylate, mefranal, SCLAREOLATE®, Syvertal, piperitenone, herbac, Milk Lactone, Menthone glycerol ketal, alpha-terpineol, Alpha Terpineol Supra, majantol, terpineol, methyl-beta-naphthyl ketone, Octanenitrile, trans-Ocimenone, Peacholide, Rosyrane Super, delta-undecalatone FCC, Romascone, 4-Carvomenthenol, Terpinenol-4, Cinnamyl propionate, 2-sec-butyl cyclo hexanone, menthone glycerin acetal, carvacrol, Thymol Crystals, anethole USP, t-anethole, bromstyrol, methyl heptane carbonate, LRG, thenyl ethyl methyl ethyl carbinol, Allyl phenethyl ether, dihyro myrcenol, rhubofix, Hydrocitronitrile, cyclopentol HC, LRG, perilla alcohol, 2,6-Octadienal-3,7-dimethyl-(E)-citral, Phenethyl butyrate, (R)-(+)-Pulegone, Isocyclogeraniol, cuminic aldehyde, iso-butyl phenyl acetate, 1,4-Cineole, FG, melonal, Estragol Ex Badiane, Petiole, rossitol, (+)-D-Menthol, d-Neomenthol, laevo menthol, menthol, natural, Menthol Racemic, neo-Menthol, 2,2,5-Trimethyl-4-hexenal, Isopropyl Quinoline, mayol, ethyl oenanthate, Hexyl propionate, Amyl butyrate, mixture of isomers, CIS 3 hexenyl butyrate, 2 Nonen-1-al, Nonenal, isomenthone, Isomenthone, menthone racemic, floropal, 1-Hepten-1-ol, 1-acetate, (R)-gamma-Undecalactone, (S)-gamma-Undecalactone, Undecalactone, Jasmatone, Dihydro Cyclacet, 5-phenyl-3-methyl-2-pentenonitril, Citronitril, isodihydro landulal FCC, 7-Ethoxy-3,7-dimethyl-octanal, gamma-Terpineol, ROSALVA, Tetrahydrojasmone, Damascol 4-,6-hydroxydihydrotheaspirane, 2-Nonanol, phenyl ethyl iso-butyrate, octyl aldehyde, Muguol, Violet Nitrile, Orivone, p-tert-amylcyclohexanol, Verdalia A, Vivaldie, lactojasmone, Benzyl isovalerate, coranol, laevo-linalool, linalool, S)-(+)-Linalool, 2-nonanone, rhuboflor, tetrahydro linalool, tetrahydro muguol, tetrahydro-4 methyl-2-phenyl-2-pyran, Phenylethyl methacrylate, Reseda Body, 4-Chloro-3,5-Xylenol, verdyl propionate, (±)-Lavandulol, (R)-(−)-Lavandulol, Gelsone, dimethyl benzyl carbonyl acetate, Isoamyl angelate, cyclemax, citrowanil B, pelargene, allyl caproate, Para Tertiary Butyl Phenol, spiro[furan-2(3H),5'-(4,7-methano-5H-indene], DECAHYDRO, Dihydroanethole, Corps Racine VS, Opalal®, ixadiene, Cumin Nitrile, methy pamplemousse, Nonadyl, Acetal R, Benzyl Cinnamate, citronellyl nitrile, jasmopyrane, 3-hexen-1-yl isovalerate, cis-3-hexenyl alpha-methyl butyrate, graniol, Methyl camomille, nerol, dimethyl octanol, cyclomethylene citronellol, Cinnamyl isobutyrate, gamma-ionone, Undecanolide, damascone gamma, Nopylaldehyde, (d)-Citronellal, (1)-Citronellal, citronellal, Mugetanol, Hexenyl tiglate, 1,2-Dihydrolinalool, dihydro-Linalool, iso-nonyl acetate, Cosmene, geranyl formate, neryl formate, furfuryl hexanoate, Cyprisate Ci, methyl octane carbonate, Isoamyl phenyl ether, 2-hexylidene cyclopentanone, 10-undecen-1-ol, rhubafuran, cyclabute, beta-naphthyl methyl ether, Heptyl acetate, Bornyl Acetate, iso-bornyl acetate, ethylene brassylate, prenyl benzoate, linalyl formate, Vetiverol, vetiverol, hexyl 2-furoate, Pomarose, Liminal, tabanon coeur, delta-damascone, Jasmonitrile, baranol, citronellol, R-(+)-B-citronellol, iso-jasmone T, parmavert, methyl iso-butyl tetrahydropyran, Rose Oxide L, Decenal-9, Octacetal, Iso Bergamate, iralia total, benzyl benzoate, gamma-Dodecalactone, cyclobutanate, fruitate, Iso Butyl Caproate, cis-4-decen-1-al-FCC, trans-4-decenal, Benzyl ether, hexyl butyrate, citronellyl oxyacetaldehyde, delta-dodecalactone FCC, butyl benzoate, cymal, florhydral, citral dimethyl acetal, Hexyl Isobutyrate, nonyl aldehyde, ethyl safranate, Methyl geraniate, Cis-3-Hexenyl Valerate, ethyl linalool, Floracetate, Methyl Cyclogeranate, Isobutyl benzoate, cyclohexyl ethyl acetate, Claritone, p-t-Butyl phenyl acetaldehyde, Para Anisyl Phenyl Acetate, Bergamal, Citronellyl Formate, Phenyl Benzoate, Dihydrojasmone, Ethyl gamma-safranate, Pivarose, Geranyl Nitrile, Cis-3-Hexenyl Tiglate, iso-butyl salicylate, ethyl damascenate, ethyl isopropyl bicycloheptene-2-carboxylate, iso-butyl quinoline, Isobutyl Quinoline-2, neobergamate forte, 4-tert-Butylbenzaldehyde, gamma-Terpinyl acetate, Dispirone, N-ethyl-2-isopropyl-5-methylcyclohexane carboxamide, 1-Methyl-3-methoxy-4-isopropylbenzene, allyl heptoate, Citral propylene glycol acetal, quincester, MUSK AMBRETTE, fenchyl acetate, Para Cresyl Phenyl Acetate, beta-Terpinyl acetate, dihydrocitronellal, Octanal, 3,7-dimethyl-, Hexyl trans-2-butenoate, methyl-2-nonenoate, dihydro-beta-ionone, Cressanther, n-butyl salicylate, nerolin bromelia, pino acetaldehyde, alpha-bisabolol, 10-undecenenitrile, octanal propylene glycol acetal, Terpinyl Methyl Ether, aphermate, Irisnitrile, phenyl ethyl tiglate, Ethyl Caprylate, glycolierral, 1,8-Thiocineol, Lavandulyl acetate, TRIFONE DIPG, beta-Ionone, ionone beta, alpha-damascene, gamma-methyl-ionone, Hexyl neopentanoate, Octyl acetate, Furfuryl heptanoate, bourgeonal, azuril, ionone alpha, Fleursandol, Khusinil, maceal, Pharaone, Oxybenzone, O-Methyl linalool, Floralozone, floralozone, Andrane, geranyl acetate, neryl acetate, 3-Thujopsanone, terpinyl acetate, 4,5,6,7-Tetrahydro-3,6-dimethylbenzofuran, Methyl Diphenyl Ether, melafleur, alpha-Phellandrene, Phenethyl 2-methylbutyrate, damascenone total, Damascenone, trans-, leminile linalyl acetate, beta-pinene, Phenyl Ethyl Benzoate, Trichloromethyl Phenyl Carbinyl Acetate, camphene, Ethyl 3,7-dimethyl-2,6-octadienoate, iso-bornyl propionate, 2-Decene-1-al, Calyxol (Quest), trans-2-decenal, pivacyclene, dihydro-alpha-ionone, Menthyl formate, sabinene, Ambrinol 20T, ebanol, dupical, frleuramone, Gyrane, Prenyl Salicylate, undecavertol, undecylenic aldehyde, Benzyl phenylacetate, ambrinol, Tetrahydroionol, damascene beta, Silvial®, veloutone, 4,7-Methano-1H-inden-6-ol, 3a,4,5,6,7,7ahexahydro-8,8-dimethyl-, propanoate, alpha-Fenchene, FLORAL SUPER, galbascone, nonyl alcohol, neo-hivernal, Myrac Aldehyde, Hindinol, hindinol, (−)-Carvyl acetate, mixture of cis and trans, Isoamyl salicylate, mixture of isoamyl and 2-methyl-butyl salicylates, L-Dihydrocarvyl acetate, mixture of isomers, frutonile, 2-tert-bbutylcyclohexylocy-2-butanol, diphenyl oxide, perilla acetate, dimethyl cyclohexyl 3-butenyl ketone, poirenate, Isodamascone N, allo-ocimene, ALDEHYDE SUPRA, 2-p-Menthadiene, capric acid nat, dimethyl benzyl carbonyl butyrate, cashmeran, citronellyl acetate, Koavone, benzyl iso-eugenol, nootkatone, Butyl sulfide, Hexyl-2-Methyl Butyrate, MUSK RI, diphenyl methane, phenyl ethyl phenyl acetate, benzyl salicylate, nopyl acetate, Alicate, cinnamyl cinnamate nat, cis-3-hexenyl cis-3-hexanoate, Gamma Terpinene, 12-oxahexadecanolide, cyclohexyl salicylate, MUSK KETONE, Phenyl Ethyl Isoamyl Ether, Apritone, irone alpha refined, para-cymene, fleuranil, ethyl-2,4-decadienoate, (+)-alpha-pinene, alpha-pinene, L-alpha-pinene, Methyl diphenyl ether, Brahmanol, Spirambrene, cis-3-hexenyl benzoate, alpha-Methyl Ionone, b-methyl ionone, Herbavert, cis-Pinane, methyl nonyl ketone, amly benzoate, Rholiate, Mefloral, P.T.BUCINAL, Wolfwood, Geranyl Propionate, givescone, ally cyclohexane propionate, peonile, nectaryl, linalyl propiononat, Terpinyl propionate, amyl salicy, beta-isomethyl ionone, boronal, oxalide T, hexyl tigilate, 3-Carene, aurantiol, ionone, gamma methyl, Datilat, decyl aldehyde, phenafeur, alpha-Sinensal, Ethyl nonanoate, 7-Methyloctyl acetate, abierate CN, Isobornyl isobutyrate, (E)-β-Ocimene, cis Ocimene, Ocimene, Neocaspirene Extra, methyl octyl acetaldehyde, spirogalbanone, Nirvanol, polysantol, 2-Heptyl tetrahydrofuran, velontal, etaspirene, 2-nonanone propylene glycol acetal, Citryl acetate, grisalva, Belambre, cis-3-hexenyl salicylate, Vetikol Acetate, Pinyl Iso Butyrate Alpha, 2-Undecene-1-al, Rhodalione, Citronellyl ethyl ether, alpha-Vetivone, Spathulenol, Citrathal, myrcene, Citronellyl Propionate, javanol, laevo trisandol, Elintaal Forte, terpineolene, octalynol, alpha-Terpinene, thesaron, Nebulone, Theaspirane, mixture of cis and trans, 1-Limonene Natural, orange oil cold pressed, orange terpenes, Precyclemone B, linaly iso-butyrate, bigarade oxide, p-Cresyl n-hexanoate, furfuryl ocanoate, Rosamusk, Elemol, iso-bornyl cyclohexanol, sinensal, natural mixture of alpha- and beta-4-tert-butyl cyclohexyl acetate, Menthanyl Acetate, verdox, Verdox HC, Vertenex, healingwood, geranyl iso-butyrate, neryl iso-butyrate, α-Amylcinnamyl alcohol, mixture with Amyl hydrocinnamyl alcohol, sandalore, ethyl-2-tert-butylcyclohexyl carbonate, Linalyl butyrate, Mandaril, cedrol, (+)-D-Menthyl acetate, Isomenthyl acetate, menthyl acetate, Salviac, Myraldyl acetate, beta-Vetivone, indolene, Cetonal, Ysamber K, Dibenzyl, Caryolan-1-ol, Geranyl Butyrate, Dihydro Ambrate, Amyl Cinnamate, Tetrahydro Geranyl Acetate, Guaiol, amyl cinnamic aldehyde, beta-santalol, Hexyl hexanoate, beta-Himachalene oxide, romandolide, Palisandal, 3,6-Dimethyl-3-octanyl acetate, tetrahydro linalyl acetate, undecyl aldehyde, Myrrhone, β-Bisabolol, oncidal, Bulnesol, I-Citronellyl Isobutyrate, Nonyl Acetate, Ethyl Undecylenate, hexalon, Cassiffix, lauric acid (natural), Dibutyl_o-phthalate, tau-Cadinol, A-cadinol, T-Muurolol, 1-Citronellyl n-Butyrate, oxyoctaline formate, alpha-Agarofuran, (e,e)-farnesol, ISO E SUPER OR WOOD, Boisiris®, Viridifloral, octyl-2-furoate, MUSK TIBETENE, nerolidol, habanolide, geranly tiglate, Hexyl benzoate, FIF/UL Mandarinal, exaltenone, CEDROXYDE®, alpha-santalol, Hydroxymethyl-isolongifolene in dipropylene glycol, 10-epi-gamma-Eudesmol, hexyl salicylate, γ-Eudesmol, phenyl acetaldehyde dimethyl acetal, galbanolene super, Ambrocenide, (Z)-4-dodecen-1-al, norlimbanol, ACALEA TBHQ, geranyl valerate, hexyl cinnamic aldehyde, agrumea, Agrumea, Isoamyl octanoate, (E)-5-Tangerinol, (Z)-5-Tangerinol, (Z)-3-Dodecenal, Kusunol, Undecene 2 Nitrile, 7-epi-alpha-Eudesmol, alpha-Eudesmol, cedryl formate, methyl cedrylone, Operanide, Ozofleur, TRIMOFIX O, Lauryl alcohol, sclareol, methyl nonyl acetaldehyde, Ethyl Caprate, cyclopentadecanone, 1,3-Dioxane, 2-(2,4-dimethyl-3-cyclohexen-1-yl)-5-methyl-5-(1-methylpropyl)-, I-Citronellyl Tiglate, butylated hydroxy toluene, cedryl methyl ether, Maritima, 1-Methyl-4-(1-methylethyl)-cyclohexane, p-Menthane, lauric aldehyde, ambronat, cetalox, clonal, linalyl anthranilate, Palisandin, 2,6,10-Trimethylundecanal, Nirvanolide, 2-tridecenal (high trans) FCC, delta muscenone, Serenolide®, 5-cyclohexadecen-1-one, Adoxal, Amberketal IPM, SANTALEX T, BOISAMBRENE FORTE, EXALTOLIDE TOTAL, Parsol MCX, alpha-Curcumene, Curzerene, vetiveryl acetate, helvetolide, 1,1,2,3,3-Pentamethylindan, Phantolid Crystals, β-Selinene, methyl nonyl acetaldehyde dimethyl acetate, Decanal diethyl acetal, CEDAC, Celestolide, alpha-Cubebene, alpha-amylcinnamyl acetate, Dodecanal dimethyl acetal, cyclohexadecenone, N-Decyl Propionate, linalyl benzoate, hydroxyambran, Citronellyl benzoate, geranyl phenyl acetate, geranyl phenylacetate, beta-Patchoulline, 2-tridcenenitrile, alpha-farnesene, caryophyllene acetate, farnesyl acetate, gernyl benzoate FCC, Acetoxymethylisolongifolene (isomers), alpha-bisabolene, Trisamber®, delta-Elemene, Cis-Iso-Ambrettolide, Oxacycloheptadec-8-en-2-one, trans-Ambrettolide, silvanone CI, ambrettolide, laevo muscone, beta-Guaiene, I-Citronellyl Phenylacetate, beta-Sesquiphellandrene, Butyl Undecylenate, Amyl Cinnamic Aldehyde Diethyl Acetal, Iso Amyl Undecylenate, Germacrene D, Amber xtreme—Compound 2, beta-Cedrene, gamma-Gurjunene, geranyl caproate, Civettone, okoumal, ethyl laurate, (−)-β-Himachalene, bisabolene, Lauryl acetate, alpha-Santalene, Decane, Valencene, tridecyl alcohol branched, 7-epi-Sesquithujene, Sclareol oxide, Vulcanolide, Selina-3,7(11)-diene, alpha-Patchoulene, trans-beta-farnesene, citronellyl caproate, β-Copaene, delta-Guaiene, 7-epi-alpha-Selinene, hexamethylindanopyran, α-Selinene, Allo-aromadendrene, isopropyl laurate, Thujopsene, γ-Cadinene, γ-Muurolene, Germacrene B, a-caryophyllene, Amber Xtreme, alpha-Amorphene, alpha-Muurolene_2, α-Cadinene, Hexyl octanoate, γ-Himachelene, α-Bergamotene, aldehyde C-14 myristic, Indolene, α-Gurjunene, Decyl anthranilate, Myristo nitrile, P.T. bucinal methyl anthranilate, caryophyllene extra, hexahydrofarnesyl acetone, alpha-Himachalene, Geranyl linalool (all trans), Cyclotetradecane, Methyl myristate, Isoamyl laurate, 1-Hexadecanol, geranly caprylate, linalyl octanoate, methyl linoleate, Ethyl myristate, iso-propyl myristate, benzyl laurate, Methyl Palmitate, ethyl palminate, isopropyl palmitate NF, Methyl stearate, Butyl stearate, hexarose, and mixtures of two, three, four or more thereof.

Preferably, the first and second malodor suppressants of the two-component system are selected from the group consisting of isopropylmyristate, galaxolide, habanolide, Operanide, Okoumal, Silkolide, Musk Plus, Helvetolide, Romandolide, Celestolide or a mixture of three, or four or more thereof.

It can be preferred that the first malodor suppressant of the two-component system is selected from the group consisting of Galaxolide, Operanide, Okoumal, habanolide and isopropylmyrstate, or mixtures of isopropylmyristate and galaxolide or isopropylmyristate and Okoumal or isopropylmyristate and Operanide or isopropylmyristate and habanolide or galaxolide and Operanide or galaxolide and habanolide.

It can be preferred that the second malodor suppressant of the two-component system is selected from the group consisting of Galaxolide, Operanide, Okoumal, habanolide and isopropylmyrstate, or mixtures of isopropylmyristate and galaxolide or isopropylmyristate and Okoumal or isopropylmyristate and Operanide or isopropylmyristate and habanolide or galaxolide and Operanide or galaxolide and habanolide.

The most preferred combinations of first and second malodor suppressant in the two-component system are combinations of isopropylmyristate and galaxolide or isopropylmyristate and Okoumal or isopropylmyristate and Operanide or isopropylmyristate and habanolide or galaxolide and Operanide or galaxolide and habanolide.

The two-component malodor suppressant system (c) comprises the first and the second malodor suppressant. The two-component malodor suppressant system may comprise only the first and the second malodor suppressant. However, the two-component malodor suppressant system may comprise further malodor suppressants which are different from the first and second malodor suppressant. The two-component suppressant system may for example comprise one further malodor suppressant, or a combination of two further malodor suppressants, or a combination of more than two, e.g., three, four, five or six different three, four, five or six, different further malodor suppressants. It may be preferred that at least one, preferably all, of the further malodor suppressants are liquid at 23° C. and 1013 mbar. It may be preferred that the malodor suppressants comprised in the malodor suppressant system form a solution upon mixing.

Preferably, the composition comprises the malodor suppressant system (c) in an amount of from 0.05 to 70 wt.-%, based on the total weight of the composition, for example 0.1 to 5 wt.-%, more preferably 0.2 to 2 wt.-%.

It may be preferred that the malodor suppressant system (c) comprises the first and second malodor suppressants in a ratio of from 0.1:99.9 to 99.9:0.1, for example from 1:99 to 99:1, more preferably from 70:30 to 30:70.

The hair shaping composition can be present in the form of an aqueous solution or an emulsion, as well as in a thickened form on an aqueous basis, particularly as a cream, gel, or paste. It is also possible to fill these compositions into aerosol cans under pressure and to release them as aerosol foam. Preferably, the fixing composition is an aqueous solution or emulsion.

The hair shaping composition of the present invention preferably has a viscosity at 25° C. of about 0.3 mPas to about 200 mPas, preferably from about 0.5 mPas to about 50 mPas, more preferably from about 0.7 mPas to about 5 mPas. The viscosity is determined—if not otherwise defined—by HAAKE Rotation Viscometer VT 550 with cooling/heating vessel and sensor systems according to DIN 53019 (MV-DIN, SV-DIN), at a shear rate of 12.9 s$^{-1}$.

Additives

The composition preferably comprises one or more further component s selected from care ingredients, waxes, emulsifiers and buffers.

"Care ingredients" according to the present invention are all compounds known to provide at least one functionality for improving the properties of the hair. Preferably, a care ingredient is a compound that provides at least one functionality for improving the cleanliness, volume, shine, color, smoothness, moisture, odor, strength, health, protection, combability or flexibility of the hair and health or sensation of the scalp. The care ingredients may be selected from the group consisting of liquid oils and fats such as avocado oil, tsubaki oil, turtle oil, Macademia nuts oil, corn oil, mink oil, olive oil, rape seed oil, yolk oil, sesame oil, parsic oil, wheat germ oil, sasanqua oil, castor oil, linseed oil, safflower oil, cotton seed oil, perilla oil, soybean oil, peanut oil, tea seed oil, kaya oil, rice bran oil, Chinese Lung oil, Japanese lung oil, hohoba oil, germ oil, triglycerine, trioctanoic acid glycerine, triisopalmitic acid glycerine; solid fats such as cacao fat, coconut oil, horse fat, hardened coconut fat, palm oil, tallow, sheep fat, hardened tallow, palm kernel oil, jojoba oil, lard, ox bone fat, wood wax kernel oil, hardened castor oil; lanolin, kapok wax, lanolin acetate, liquid lanolin, isopropyllanolin fatty acid, hexyllaurate, reduced lanolin, hard lanolin, POE lanolin alcohol ether, POE lanolin alcohol acetate, POE cholesterol ether, lanolin fatty acid polyethylene glycol, POE hydrogenated lanolin alcohol ether; hydrocarbons nonvolatile hydrocarbons and hydrocarbon esters such as fluid paraffin, solid paraffin, vaseline, ozocerite, squalane, pristan, ceresin, squalane, petrolatum, mineral oil, isododecane, microcrystalline wax; fatty acid oils, ester oils such as cetyl octanoate, isopropyl myristate; betaine, carnitin, carnitin esters, creatine, amino acids, peptides, proteins, vitamines, phospholipides, e.g. lecithins or ceramides. Useful are also quaternary benzyl salts such as lauryl-dimethylethylbenzyl-ammonium chloride (QUATERNIUM-14); imidazolidinyl derivatives as for example CTFA: QUATERNIUM-87 (Rewoquat® W 575 of Witco, Germany); N-(3-chloroallyl)hexaminium chloride (QUATERNIUM-15); a quaternary ammonium compound sold under the trade name Finquat CT by the company Finetex (CTFA: QUATERNIUM-75; see CTFA Tenth Edition, page 1604), and volatile or nonvolatile, soluble or insoluble silicones. By soluble what is meant is that the silicone is miscible with the aqueous carrier of the composition so as to form part of the same phase. By insoluble what is meant is that the silicone forms a separate, discontinuous phase from the aqueous carrier, such as in the form of an emulsion or a suspension of droplets of the silicone. Soluble silicones include silicone copolyols, such as dimethicone copolyols, e.g. polyether siloxane-modified polymers, such as polypropylene oxide, polyethylene oxide modified polydimethylsiloxane, wherein the level of ethylene and/or propylene oxide sufficient to allow solubility in the composition. Preferred, however, are insoluble silicones. The insoluble silicone hair conditioning agent for use herein preferably has viscosity of from about 1,000 to about 2,000,000 mPas at 25° C., more preferably from about 10,000 to about 1,800,000 mPas, even more preferably from about 100,000 to about 1,500,000 mPas. The viscosity can be measured by means of a glass capillary viscometer as set forth in Dow Corning Gorparate Test Method CTM0004, Jul. 20, 1970. Examples are polyalkyl siloxanes, polyaryl siloxanes, polyalkylaryl siloxanes, polyether siloxane copolymers, dimethylpolysiloxane containing terminal hydroxyl groups, methylphenyl polysiloxane containing terminal hydroxyl groups and mixtures thereof, low molecular weight oligomeric polydimethylsiloxane or cyclic polydimethylsiloxane, polyether siloxane copolymers, Silicone conditioning polymers that are specially preferred are CTFA: dimethicone bisaminoo hydroxypropyl copolyol, bisamino PEG/PPG-41/3 aminoethyl PG-propyl dimethicone, dihydroxy-polydimethylsiloxane (CTFA: dimethiconol). Also preferred are volatile silicones such as e.g. CTFA: dimethicone, dimethicone copolyol and cyclodimethicone. Preferably, the care ingredients are selected from the group consisting of Polyquaternium-6, Polyquaternium-9, mineral oil, petrolatum and dimethicone. The amount of the above care ingredient preferably ranges from about 0.01 to 30 wt.-%, better still from about 0.05 to 15 wt.-%, and most preferred from about 0.1 to 5 wt.-%, based on the total weight of the composition.

The composition may further comprise waxes. For example, the wax may be beeswax, apple wax, canderilla wax, cotton wax, carnauba wax, bayberry wax, insect wax, whale wax, montan wax, rice bran wax, kapok wax, cane wax, jojoba wax, and shellac wax. The wax may also be a fatty alcohol. The fatty alcohol may be selected from the group consisting of linear and/or branched C12 to C30 fatty alcohols; e.g., from the group consisting of cetyl alcohol, stearyl alcohol, cetearyl alcohol, behenyl alcohol, any mixtures of two, three or more thereof. The composition may comprise the wax in an amount of from 0.1 to 20 wt.-%, or from 0.2 to 15 wt.-%, or from 0.5 to 11 wt.-%, based on the total weight of the composition.

The composition preferably further comprises an emulsifier. The amount of emulsifiers in the composition is preferably in the range of from about 0.01 to about 10 wt.-%, and more preferably from about 0.1 to about 5 wt.-%, based on the total weight of the composition. Emulsifiers according to the present invention are for example selected from PEG(40) hydrogenated castor oil, PEG(35) castor oil, coceth-10 and ceteareth-25.

The composition preferably comprises a buffer. Generally all buffers providing a desired pH value can be used. It may be preferred in the present invention that one component of the buffer is the same as the alkalizing agent. Preferably, the buffer is an $NH_3/(NH_4)_2CO_3$ buffer. For example, the buffer is an $NH_3/(NH_4)_2CO_3$ buffer and the alkalizing agent comprises $NH_3$.

The composition may further comprise one or more additive selected from cationic polymers, hair swelling and penetration enhancing substances, disulfides, cationic surfactants, perfumes, plant extracts, or combinations of two or more thereof.

Cationic polymers may for example be cationic copolymers, cationic polysaccharides or cationic silicon polymers comprising quaternary nitrogen groups. The preferred quantity for use of the cationic polymers is from about 0.05 to about 15 wt.-%, more preferably from about 0.1 to about 8 wt.-%, and most preferred from about 0.2 to about 3 wt.-%, based on the total weight of the composition.

Suitable cationic copolymers are made by copolymerizing cationic monomers comprising quaternary nitrogen groups, and non-cationic monomers. Suitable cationic monomers are unsaturated, radical polymerizable compounds carrying at least one cationic group, particularly ammonium-substituted vinyl monomers such as trialkyl methacryl oxyalkyl ammonium, trialkyl acryloxyalkyl ammonium, dialkyl diallyl ammonium, and quaternary vinyl ammonium monomers with groups containing cyclic, cationic nitrogen such as pyridinium, imidazolium, or quaternary, e.g. alkyl vinyl imidazolium, alkyl vinyl pyridinium, or alkyl vinyl pyrrolidone salts. The alkyl groups of these monomers are preferably lower alkyl groups, such as C1 to C7 alkyl groups, with C1 to C3 alkyl groups being especially preferred. The ammonium group-containing monomers can be copolymerized with non-cationic monomers. Suitable comonomers are, for example, acrylamide, methacrylamide, alkyl- and dialkyl acrylamide, alkyl- and dialkyl methacrylamide, alkyl acrylate, alkyl methacrylate, vinyl caprolactone, vinyl caprolactam, vinyl pyrrolidone, vinyl ester, e.g. vinyl acetate, vinyl alcohol, propylene glycol, or ethylene glycol, wherein the alkyl groups of these monomers are preferably C1 to C7 alkyl groups, with C1 to C3 alkyl groups being especially preferred.

Suitable cationic polysaccharides comprising quaternary nitrogen groups are for example cationic derivatives of cellulose, starch or guar, chitosan and chitosan derivatives.

Suitable cationic silicon polymers may be of the general formula

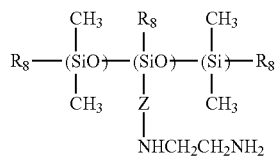

wherein $R_8$=OH or $CH_3$ and Z represents the propyl, isopropyl or isobutyl group.

So-called swelling agents and penetrating substances may be added to the hair shaping composition, examples being urea, melamine, ethers, e.g. dipropylene glycol monomethyl ether, 2-pyrrolidon, imidazolidin-2-one, 1-methyl-2-pyrrolidone; alkali or ammonium thiocyanate, polyvalent alcohols, isopropanol in a quantity of from about 1 to about 30 wt.-%, based on the total weight of the composition.

It is advantageous if the permanent shaping agent, to avoid making the hair too kinky, contains the disulfide of a hair keratin-reducing compound (thiol), particularly dithioglycolic acid, 2,2'dithio-bis[N-(3-hydroxypropyl)-acetamid], 2,2'-dithio-bis[N-(propyl)-acetamid], 2,2'-dithio-bis[N-(2-hydroxypropyl)-acetamid], dithiolactic acid and their salts. The preferred quantity for use is from about 0.1 to about 30 wt.-%, more preferably from about 0.5 to about 20 wt.-%, and most preferred from about 1 to about 10 wt.-%, based on the total weight of the composition. The ratio between the hair keratin-reducing agents and the disulfides is preferably from about 20:1 to about 1:2, and more preferably from 10:1 to 1:1.

Cationic surfactants that can be preferably used in the cosmetic composition of the present invention contain amino or quaternary ammonium moieties. Among the quaternary ammonium-containing cationic surfactant materials, those of the general formula $$[NR^4,R^5,R^6,R^7]^+X^-$$

are particularly preferred. Therein, $R^4$ to $R^7$ are independently an aliphatic group of from about 1 to about 22 carbon atoms or an aromatic, alkoxy, polyoxyalkylene, alkylamido, hydroxyalkyl, aryl or alkylaryl group having from about 1 to about 22 carbon atoms; and $X^-$ is a salt-forming anions such halogen, (e.g. chloride, bromide, iodide), acetate, citrate, lactate, glycolate, phosphate nitrate, sulfate, and alkylsulfate radicals.

The cosmetic compositions of the present invention may also comprise a nonvolatile low inching point fatty alcohol. The fatty alcohols hereof have a melting point of 30° C. or less, preferably about 25° C. or less, more preferably about 22° C. or less. The unsaturated fatty alcohols hereof are also nonvolatile. By nonvolatile what is meant is they have a boiling point at 1.0 atmospheres of at least about 260° C., preferably at least about 275° C., more preferably at least about 300° C. Suitable fatty alcohols include unsaturated monohydric straight chain fatty alcohols, saturated C8-C12 straight chain fatty alcohols, and mixtures thereof. The unsaturated straight chain fatty alcohols will typically have one degree of unsaturation. Di- and tri-unsaturated alkenyl chains may be present at low levels, preferably less than about 5 wt.-%, based on the total weight of the unsaturated straight chain fatty alcohol, more preferably less than about 2 wt.-%, most preferably less than about 1 wt.-%. Examples of saturated C8-C12 straight chain alcohols include octyl alcohol, caprylic alcohol, decyl alcohol, and lauryl alcohol. The low melting point fatty alcohols hereof are used at a level of from about 0.1 to about 15 wt.-%, based on the total weight of the composition, more preferably from about 0.2 to about 11 wt.-%, most preferably from about 0.5 to about 3 wt.-%.

The composition may further comprise usual and known additives for permanent hair shaping compositions. Suitable additives are for example kaolin, bentonite, fatty acids, higher fatty alcohols, starches, cellulose derivatives, alginates, polyacrylic acid and its derivatives, cellulose derivatives, alginates, vaseline, and paraffin oils; wetting agents or emulsifiers from the classes of anionic, cationic, amphoteric or nonionic surface-active substances, such as fatty alcohol sulfates, fatty alcohol ether sulfates, alkyl sulfonates, alkylbenzene sulfates, quaternary ammonium salts, alkyl betaines, ethoxylated alkylphenols, fatty acid alkanolamides or ethoxylated fatty acid esters; and opacifiers such as polyethyleneglycol esters; alcohols, such as ethanol, propanol, isopropanol; water-soluble polyhydric alcohols having two or more hydroxyl groups in the molecule. Typical examples of such polyhydric alcohols are dihydric alcohols such as ethylene glycol, 1,2- or 1,3-propanediol, 1,2-pentanediol and glycerin; further, trimethylene glycol, 1,2-butylene glycol, 1,3-butylene glycol, 1,4-butylene glycol, tetramethylene glycol, 2,3-butylene glycol, pentamethylene glycol, 2-butene-1,4-diol, hexylene glycol, octylene glycol; trihydric alcohols such as glycerin, trimethylol propane, 1,2,6-hexanetriol and the like; tetrahydric alcohols such as penthaerythritol; pentahydric alcohols such as xylytol, etc.; hexahydric alcohols such as sorbitol, mannitol; polyhydric alcohol polymers such as diethylene glycol, dipropylene glycol, polyethylene glycol, polypropylene glycol, tetraethylene glycol, diglycerine, polyethylene glycol, triglycerine, tetraglycerine, polyglycerine; dihydric alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether; dihydric alcohol alkyl ethers such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether; dihydric alcohol etheresters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate; glycerin monoalkyl ethers such as xyl alcohol, selachyl alcohol, batyl alcohol; sugar alcohols such as sorbitol, maltitol, maltotriose, mannitol, sucrose, erythritol, glucose, fructose, starch sugar, maltose, xylytose, starch sugar reduced alcohol, glysolid, tetrahydrofurful alcohol, POE tetrahydrofurfuryl alcohol, POPbutyl ether, POP POE butyl ether, tripolyoxypropylene glycerin ether, POPglycerin ether, POPglycerin ether phosphoric acid, POP POE pentanerythritol ether; sugars such as D-glucose; solubilizers, stabilizers, buffer substances, perfume oils, dyes, and hair-conditioning and haircare ingredients such as lanolin derivatives, cholesterol, pantothenic acid, and betaine.

The composition may comprise nonionic surfactants, preferably those having an HLB (Hydrophilic Lipophilic Balance) of greater than 12. Preferred nonionic surfactants with HLB>12 may be, for example, an ethoxylated or ethoxylated/propoxylated fatty alcohol with a fatty chain comprising from 12 to 22 carbon atoms, ethoxylated sterols, such as stearyl- or lauryl alcohol (EO-7); PEG-16 soya sterol or PEG-10 soya sterol, polyoxyethylene polyoxypropylene block polymers (poloxamers) and their mixtures. Ethoxylated sterols and of poloxamers are preferred. The nonionic surfactant of HLB<8 can be chosen in particular frons glyceryl esters, such as mono-, di- or triglyceryl mono-, di- or triisostearate or -oleate, sugar esters, such as sucrose or methyl glucose mono- or diisostearate or -oleate, alkylpolyglucoside ethers, such as sorbitan isostearate, oleyl- or isostearylpolyglucoside; polyoxyethylene (20) sorbitan monostearate (CTFA: Polysorbat-60), and their mixtures. Sugar esters and alkylpoly-glucoside ethers are preferred. The amount of nonionic surfactant is preferably in the range of from about 0.1 to about 5 wt.-%, and more preferably from about 1 to about 3 wt.-%, based on the total weight of the composition.

The cosmetic compositions herein can contain a variety of other optional components suitable for rendering such compositions more cosmetically or aesthetically acceptable or to provide them with additional usage benefits. Such conventional optional ingredients are well-known to those skilled in the art. The composition of the invention may thus comprise lipophilic or hydrophilic adjuvants which are standard in the cosmetics or dermatological fields, such as surfactants, in particular foaming surfactants, preservatives, antioxidants, sequestering agents, solvents, fragrances, fillers, screening agents, odor absorbers, coloring materials and lipid vesicles. A wide variety of additional ingredients can be formulated into the present cosmetic composition. These include: hair-hold polymers, detersive surfactants such as anionic, nonionic, amphoteric, and zwitterionic surfactants; additional thickening agents and suspending agents, such as xanthan gum, guar gum, starch and starch derivatives, viscosity modifiers such as methanolamides of long chain fatty acids, coco monoethanol amide, salts such as sodium potassium chloride and sulfate and crystalline suspending agents, and pearlescent aids such as ethylene glycol distearate; UV-filters and sunscreens, e.g. such as p-methoxy cinnamic acid isoamylester, lipophile cinnamic acid esters, salicylic acid esters, 4-amino benzoic acid derivatives or hydrophilic sulfonic acid derivatives of benzophenones or 3-benzyliden camphers; antioxidants such as tocopheroles; agents for combating free radicals; preservatives such as benzyl alcohol, methyl paraben, propyl paraben and imidazolidinyl urea; polyvinyl alcohol; pH adjusting agents, such as citric acid, formic acid, glyoxylic acid, acetic acid, lactic acid, pyruvic acid, sodium citrate, succinic acid, phosphoric acid, sodium hydroxide, sodium carbonate; salts, in general, such as potassium acetate and sodium chloride; coloring agents, such as any of the FD&C or D&C dyes; perfumes, sequestering agents, such as disodium ethylenediamine tetraacetate, and polymer plasticizing agents, such as glycerin, disobutyl adipate, butyl stearate, and propylene glycol. The additives are preferably used in quantities usual for such purposes; for example, the wetting agents and emulsifiers each in concentrations of a total of 0.2 to 30 wt.-%, the alcohols in a total quantity of 0.1 to 20 wt.-%, the opacifiers, perfume oils and dyes each in a quantity of 0.01 to 1 wt.-%, the buffer substances in a total quantity of 0.1 to 10 wt.-%, and sugars, stabilizers and hair-conditioning and hair-care ingredients each in a quantity of 0.1 to 5 wt.-%, thickeners and solubilizers each in a quantity of 0.5 to 20 wt.-%, based on the total weight of the composition. Surfactants are preferably contained at levels of from about 0.1 to about 5 wt.-%, more preferably from about 0.2 to about 1.5 wt.-%, most preferably from about 0.4 to about 0.8 wt.-%, based on the total weight of the composition.

It may be preferred that the composition comprises
(a) 1-11 wt.-% of the reducing agent comprising a mercapto functional group,
(b) 0.2-5 wt.-% of the alkalizing agent, and
(c) 0.1-70 wt.-% of the malodor suppressant system.

According to a preferred embodiment of the present invention, a permanent shaping composition for permanent waving of the hair comprises 1-11 wt.-% of a reducing agent (a) selected from the group consisting of ammonium thioglycolate and cysteine,
0.2-5 wt.-% of an alkalizing agent (b) selected from the group consisting of ammonia, monoethanolamine and ammonium bicarbonate,
0.1-70 wt.-% of a malodor suppressant system (c) selected from the group consisting of isopropylmyristate/galaxolide, isopropylmyristate/Okoumal. Isopropylmyristate/Operanide, isopropylmyristate/habanolide, galaxolide/Operanide and galaxolide/habanolide,
0.05-5 wt.-% of care ingredients selected from the group consisting of polyquaternium-6, polyquaternium-9, mineral oil, petrolatum and dimethicone,
0-5 wt.-% of wax selected from the group consisting of cetearyl alcohol, stearyl alcohol and beeswax,
0-5 wt.-% emulsifier selected from the group consisting of PEG(40) hydrogenated castor oil, PEG(35) castor oil, coceth-10 and ceteareth-25,
0-2 wt.-% of a buffer, and
water,
wherein the wt.-% are based on the total weight of the composition.

According to a preferred embodiment of the present invention, a permanent shaping composition for permanent waving of the hair comprises 1-11 wt.-% of a reducing agent (a) selected from the group consisting of ammonium thioglycolate and cysteine,
0.2-5 wt.-% of an alkalizing agent (b) selected from the group consisting of ammonia, monoethanolamine and ammonium bicarbonate,
0.1-70 wt.-% of a malodor suppressant system (c) selected from the group consisting of Galaxolide, Operanide, Okoumal, habanolide and isopropylmyrstate,
0.05-5 wt.-% of care ingredients selected from the group consisting of polyquaternium-6, polyquaternium-9, mineral oil, petrolatum and dimethicone,
0-5 wt.-% of wax selected from the group consisting of cetearyl alcohol, stearyl alcohol and beeswax,
0-5 wt.-% emulsifier selected from the group consisting of PEG(40) hydrogenated castor oil, PEG(35) castor oil, coceth-10 and ceteareth-25,
0-2 wt.-% of a buffer, and
water,
wherein the wt.-% are based on the total weight of the composition.

According to a preferred embodiment of the present invention, a permanent shaping composition for straightening of the hair comprises 2-11 wt.-% of a reducing agent (a) selected from the group consisting of ammonium thioglycolate and cysteine,
0.2-5 wt.-% of an alkalizing agent (b) selected from the group consisting of ammonia, monoethanolamine and ammonium bicarbonate,
0.1-70 wt.-% of a malodor suppressant system (c) selected from the group consisting of isopropylmyristate/galaxolide, isopropylmyristate/Okoumal, Isopropylmyristate/Operanide, isopropylmyristate/habanolide, galaxolide/Operanide and galaxolide/habanolide,
0.05-5 wt.-% of care ingredients selected from the group consisting of polyquaternium-6, polyquaternium-9, mineral oil, petrolatum and dimethicone,
0-5 wt.-% of wax selected from the group consisting of cetearyl alcohol, stearyl alcohol and beeswax,
0-5 wt.-% emulsifier selected from the group consisting of PEG(40) hydrogenated castor oil, PEG(35) castor oil, coceth-10 and ceteareth-25,
0-2 wt.-% of a buffer,
0-5 wt.-%, of oily products selected from the group consisting of perfumes, jojoba oil and plant extracts, and
water,
wherein the wt.-% are based on the total weight of the composition.

According to a preferred embodiment of the present invention, a permanent shaping composition for straightening of the hair comprises 2-11 wt.-% of a reducing agent (a) selected from the group consisting of ammonium thioglycolate and cysteine,
0.2-5 wt.-% of an alkalizing agent (b) selected from the group consisting of ammonia, monoethanolamine and ammonium bicarbonate,
0.1-70 wt.-% of a malodor suppressant system (c) selected from the group consisting of Galaxolide, Operanide, Okoumal, habanolide and isopropylmyrstate,
0.05-5 wt.-% of care ingredients selected from the group consisting of polyquaternium-6, polyquaternium-9, mineral oil, petrolatum and dimethicone,
0-5 wt.-% of wax selected from the group consisting of cetearyl alcohol, stearyl alcohol and beeswax,
0-5 wt.-% emulsifier selected from the group consisting of PEG(40) hydrogenated castor oil, PEG(35) castor oil, coceth-10 and ceteareth-25,
0-2 wt.-% of a buffer,
0-5 wt.-% of oily products selected from the group consisting of perfumes, jojoba oil and plant extracts, and
water,
wherein the wt.-% are based on the total weight of the composition.

The second aspect of the present invention is a kit for the permanent deformation of hair comprising A. an individually packaged composition comprising
  (a) at least one reducing agent comprising a mercapto functional group, and
  (b) at least one alkalizing agent;
B. an individually packaged malodor suppressant system (c) comprising at least a first malodor suppressant wherein the first malodor suppressant has a molecular weight of from 100 to 400 g/mol, and wherein the malodor suppressant system has a distribution coefficient log P (octanol/water) of 2 or more; and
C. optionally, an individually packaged fixing composition comprising an oxidizing agent.

"Individually packaged" means that the components may be packaged in separate containers or in compartmented containers without being in contact with each other.

In the kit for the permanent deformation of hair according to the present invention, the carrier, the reducing agent (a), the alkalizing agent (b) and the malodor suppressant system (c) are in accordance with the carrier, reducing agent (a), alkalizing agent (b) and malodor suppressant system (c) described with regard to the first aspect of the invention. In particular, the malodor suppressant system may be a one-component malodor suppressant system or a two-component malodor suppressant system. The malodor suppressant of the one-component malodor suppressant system is preferably selected from the group consisting of Galaxolide, Operanide, habanolide and isopropylmyrstate. The malodor suppressants of the two-component malodor suppressant system are preferably selected from the group of compounds described above and named "list of malodor suppressants".

The kit may also comprise a further component C. Component C is a composition for oxidatively post-treating (fixing) the hair comprising an oxidizing agent.

Any known oxidizing agents that have been used before in fixing compositions can be used for the fixation. Examples of such oxidizing agents are potassium bromate, sodium bromate, sodium perborate, dehydroascorbic acid, urea peroxide, hydrogen peroxide, and inorganic peroxygen materials capable of yielding hydrogen peroxide in an aqueous solution. Such materials are for example inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, or tetrahydrates. Alkyl/aryl peroxides and/or peroxidases may also be used. Mixtures of two or more such oxidizing agents can be used if desired. The oxidizing agents may be provided in aqueous solution or as a powder which is dissolved prior to use. Hydrogen peroxide is preferred.

The concentration of the oxidizing agent varies, depending on the application time and the application temperature. Generally, oxidizing agents are used in a concentration of from about 0.5 to 12 wt.-%, preferably 1 to 3 wt.-%, based on the total weight of the fixing composition.

The fixing composition can comprise other materials, for example, weak acids or peroxide stabilizers. The fixing composition may also include other substances, such as wetting agents, hair-care substances such as cationic polymers, weak acids, buffer substances or peroxide stabilizers, and may be in the form of an aqueous solution, an emulsion, or a thickened water-based form, in particular a cream, gel or paste. These typical additives may be contained in the fixing composition in a quantity of from 0.1 to 10 wt.-%, based on the total weight of the fixing composition.

The fixing composition can be present in the form of an aqueous solution or an emulsion, as well as in a thickened form on an aqueous basis, particularly as a cream, gel, or paste. It is also possible to fill these compositions into aerosol cans under pressure and to release them as aerosol foam. Preferably, the fixing composition is an aqueous solution or emulsion.

The consumer mixes the components A and B together immediately before use and applies it onto the hair. They may be mixed from 5 sec to 3 min, alternatively from 15 sec to 2 min, alternatively for 30 sec to 1 min prior application to the hair.

The present invention may be provided in a variety of packaging devices and/or dispensing devices. These dispensing devices can come in the form of separate devices which may be used independently or in combination with one another. Typically, the compositions are contained within separate single or multi-compartment containers so that the compositions can be stored separately from one another before use. For use, the compositions are dispensed from the respective device and applied to the consumer's hair by an application means.

A preferred packaging device involves storing the composition A in a first container such as a bottle, tube, aerosol, or a sachet, separately storing the malodour suppressant system in an additional compartment within the first container or more preferably in a separate container which may be identical such as a dual sachet or aerosol systems, or different such as a bottle and tube system. Any combination may be used and is typically contingent on the type of composition being stored, e.g., based on its viscosity. The compositions A and B may be mixed by any means, including by using a mixing bowl and/or a mixing tool, by adding one component into the container of the other component followed by mixing, by perforating or displacing a seal located between the separate compartments of the components within a single container or sachet followed by mixing. As an alternative, the compositions A and B can be mixed directly in the hair or on the head of a consumer.

The devices described herein above can also be used in combination with a product delivery and or application tool to aid application of the product onto the hair, including using a nozzle attached to one of the containers, using a separate applicator device such as a comb or brush, using a comb attached to or instead of the dispensing nozzle whereby the product is dispensed through hollow tines and dispensing apertures located in the comb tines. The application devices may also include devices which assist in achieving particular effects such as highlighting such as highlighting combs, brushes and tools, foils and highlighting caps. Highlighting devices comprising a hinged device into which an amount of composition is placed and then used to apply the composition to pre-determined/selected hair strands may also be used. Additional device technology can be used to assist in the penetration of the product into the hair. Examples of such technology include heating devices, ultraviolet light devices and ultrasound devices.

The permanent shaping and fixing compositions, may be manufactured by conventional processes known in the art for manufacturing permanent shaping and fixing products, e.g., by ad-mixing the ingredients of each composition in suitable vessels, followed by packaging in appropriate individual containers.

The third aspect of the present invention is a method for the permanent deformation of hair comprising the following steps:
 i. providing a permanent shaping composition by mixing
  (a) at least one reducing agent comprising a mercapto functional group,
  (b) at least one alkalizing agent, and
  (c) a malodor suppressant system comprising at least a first malodor suppressant, wherein the first malodor suppressant has a molecular weight of from 100 to 400 g/mol, and wherein the malodor suppressant system has a distribution coefficient log P (octanol/water) of 2 or more;
 ii. applying the permanent shaping composition to the hair before or after putting the hair in a desired shape;
 iii. allowing the permanent shaping composition to act on the hair for a predetermined acting time sufficient for the permanent shaping of the hair;
 iv. rinsing the hair with water;
 v. applying to the hair a fixing composition comprising an oxidizing agent for performing an oxidative post-treatment of the hair; and
 vi. rinsing the hair with water.

In the method for the permanent deformation of hair according to the present invention, the carrier, the reducing agent (a), the alkalizing agent (b) and the malodor suppressant system (c) are in accordance with the carrier, reducing agent (a), alkalizing agent (b) and malodor suppressant system (c) described with regard to the first aspect of the invention. In particular, the malodor suppressant system may be a one-component malodor suppressant system or a two-component malodor suppressant system. The malodor suppressant of the one-component malodor suppressant system is preferably selected from the group consisting of Galaxolide, Operanide, Okoumal, habanolide and isopropylmyrstate. The malodor suppressants of the two-component malodor suppressant system are preferably selected from the group of compounds described above and named "list of malodor suppressants". Further, the fixing composition is in accordance with the fixing composition described with regard to the second aspect of the invention.

The method comprises as a first step the provision of a permanent shaping composition. Said composition is provided by mixing at least one reducing agent (a), at least one alkalizing agent (b) and a malodor suppressant system (c).

The components (a) to (c) may be mixed at any time before use. For example, the components (a) to (c) may be mixed before being packaged, so that the customer may purchase the permanent shaping composition already in mixed form. However, the components are preferably mixed immediately before use. "Use" of the composition according to the present invention means working the permanent shaping composition into the hair. "Immediately before use" according to the present invention means no more than 5 min before use. It is however preferred to acid the hair serum no more than 3 min before use, for example, no more than 2 min before use or no more than 1 min before use. It is most preferred to add the hair serum less than 1 min before use.

The components may be mixed by any means, including using a mixing bowl and/or a mixing tool, adding one component into the container of the other component followed by mixing, perforating or displacing a seal located between the separate compartments of the components within a single container or sachet followed by mixing.

Subsequently, after mixing the components as described above, the permanent shaping composition is applied to the hair.

Either before or after applying the permanent shaping composition, the hair is put into the desired shape, preferably as follows: First the hair (which is washed and towel-dried) is separated into multiple sections and then these sections are rolled onto curlers. The curlers used for permanent waves have a diameter of about 5 to 13 mm, while the curlers used for straightening must have a diameter greater than 13 mm. After the hair is rolled on curlers, the curlers are thoroughly wetted down using the permanent shaping composition. As an alternative, the hair may be thoroughly wetted down using the permanent shaping composition before being curled on the rollers, while the procedure of rolling the hair onto curlers is the same.

The permanent shaping composition is then allowed to act on the hair for a predetermined acting time sufficient for the permanent shaping of the hair. The amount of time the permanent shaping composition stays on the hair is from about 1 to about 30 min, preferably from about 5 to about 20 min. This time can be shortened by adding heat via the use of a heat radiator or a hood dryer. This time is dependent from the hair quality, the pH value, the shaping effectiveness of the color-providing shaping agent, the desired level of change as well as on the application temperature.

The hair is then rinsed with water.

As a further step, the method comprises the application of a fixing composition comprising an oxidizing agent for performing an oxidative post-treatment of the hair. Depending on the hair thickness and length, the amount of fixing composition, the application time and the application temperature can vary. Preferred application times are in the range of from 1 to 40 min, for example 2 to 20 min, more preferably 5 to 10 min. Preferred application temperatures are in the range of from 25 to 40° C.

After the oxidative post-treatment, the hair is rinsed with water. The curlers may be removed from the hair at any time after the oxidative post-treatment, preferably before the hair is rinsed with water.

As a fourth aspect, the present invention relates to the use of a malodor suppressant system comprising a first malodor suppressant, a second malodor suppressant, and, optionally, one or more further malodor suppressants, wherein the first malodor suppressant is different from the second malodor suppressant, wherein each of the first and second malodor suppressants have a molecular weight of from 100 to 400 g/mol, and wherein the malodor suppressant system has a distribution coefficient log P (octanol/water) of 2 or more, in a composition for the treatment of hair, especially in a permanent shaping composition for the permanent deformation of hair.

The malodor suppressant system used according to this aspect of the invention is in accordance with the malodor suppressant system (c) described with regard to the first aspect of the invention.

EXAMPLES

In order to determine the influence of the malodor suppressant systems on different permanent shaping compositions, test samples were provided and analyzed.

| Permanent shaping premix | |
|---|---|
| Raw Material | wt.-% |
| Water purified | qs |
| Ammonium thioglycolate, 59.3% [1] | 10.8 |
| Ammonium hydroxide, 25% [1] | 1.4 |
| Ammonium bicarbonate | 2 |
| Coceth-10 | 0.8 |
| PEG-35 castor oil | 1.2 |
| Hydroxyethyl cellulose | 0.8 |
| Polyquaternium-6 | 2 |
| urea, USP | 2.35 |
| D,L-carnitine hydrochloride | 0.31 |

[1] in water

| | | | One-component malodor suppressant system | | | | | | |
|---|---|---|---|---|---|---|---|---|---|
| Raw material | log P (octanol/water) | density [g/mL] | S1 | S2 | S3 | S4 | S5 | S6 | C1 |
| | | | | | | wt.-% | | | |
| IPM[1] | 7.41 | 0.864 | 100 | | | | | | |
| Habanolide | 4.77 | 0.901 | | 100 | | | | | |
| Galaxolide | 5.93 | 0.946 | | | 100 | | | | |
| Operanide | 4.90 | 1.01 | | | | 100 | | | |
| Okoumal | 5.79 | 0.971 | | | | | 100 | | |

-continued

| | | | One-component malodor suppressant system | | | | | | |
|---|---|---|---|---|---|---|---|---|---|
| Raw material | log P (octanol/water) | density [g/mL] | S1 | S2 | S3 | S4 wt.-% | S5 | S6 | C1 |
| Benzyl benzoate | 3.59 | 1.129 | | | | | | 100 | |
| Dipropylene glycol | −0.62 | 1.034 | | | | | | | 100 |

[1] IPM: isopropylmyristate

| | Two-component malodor suppressant system | | | | |
|---|---|---|---|---|---|
| Raw material | D1 | D2 | D3 wt.-% | D4 | D5 |
| IPM [1] | 50 | 50 | 50 | 50 | |
| Habanolide | 50 | | | | |
| Galaxolide | | 50 | | | 50 |
| Operanide | | | 50 | | 50 |
| Okoumal | | | | 50 | |

[1] IPM: isopropylmyristate

| Fixing composition | |
|---|---|
| Raw material | wt.-% |
| Water purified | qs |
| Hydrogen peroxide | 4.5 |
| Phosphoric acid | 0.4 |
| Salicylic acid | 0.08 |
| Coco-betaine | 2.2 |
| Laureth-4 | 1.3 |
| PEG-35 castor oil | 1.2 |
| Sodium camphoacetate | 0.15 |
| PEG-40 hydrogenated castor oil | 1.2 |
| Propylene glycol | 2.5 |
| Polyquaternium-35 | 0.6 |
| Creatine | 0.28 |
| Fragrance | 0.3 |

Test Procedure 1

After wetting the hair with water, it is wound up on curlers. The permanent shaping premix are mixed with the malodor suppressant system to form the permanent shaping composition comprising the malodor suppressant system in an amount of 0.7 wt.-%. The permanent shaping composition is uniformly applied onto the hair on the curlers. The permanent shaping composition is left there for 10 min using an infrared drying hood and a temperature of 40° C. The hair is then rinsed with lukewarm water. The fixing composition is then uniformly applied to the hair and left there for 8 min. Finally, the hair is rinsed with lukewarm water and the curlers are removed.

The procedure is carried out for each of the above identified malodor suppressant systems.

As a comparative example C2, the procedure is carried out without addition of a malodor suppressant (C2). In this case, the permanent shaping premix is uniformly applied onto the hair on the curlers. The further procedure is carried out as described above.

The treated hair has a well groomed look in wet and dry condition, a good touch and fine wet combing properties. It displays a good elasticity from the tips to the root. During the treating time with the malodor suppressant systems D1 to D5 and S1 to S6, a reduced and more pleasant odor is noticed compared to using malodor suppressant system C1 or no malodor suppressant system (C2).

Test Procedure 2

A panel test was performed with 5 panelists with trained expertise in the classification of thiol malodour. The panelists received a mixture of the permanent shaping premix and 0.7 wt.-% of one malodor suppressant system, as described above (stirred by a single operator for all tests) Immediately and 25 min after mixing, the panelists were asked to rate the thiol malodor according to a scale of 0 to 5 (0=no thiol smell, 5=harsh thiol smell), the mixture being passed from panelist to panelist with an additional stirring for each of the panelists.

| | S1 | S2 | S3 | S4 | S5 | S6 | C1 | C2 |
|---|---|---|---|---|---|---|---|---|
| Odor | 3 | 4 | 1-2 | 2 | 3 | 3 | 5 | 5 |

| | D1 | D2 | D3 | D4 | D5 |
|---|---|---|---|---|---|
| Odor | 2 | 1-2 | 1 | 1-2 | 1-2 |

The same odor rating is obtained immediately after mixing and 25 min after mixing.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A permanent shaping composition for the permanent deformation of hair comprising, in a cosmetically acceptable carrier,
   (a) at least one reducing agent comprising a mercapto functional group,
   (b) at least one alkalizing agent, and
   (c) a malodor suppressant system comprising at least a first and a second malodor suppressant, the first and second malodor suppressants form the malodor suppressant system, wherein the first and second malodor suppressants are a combination of operanide and isopropyl myristate.

2. The composition according to claim 1, wherein the malodor suppressant system (c) is comprised in an amount of at least 0.05 wt % to 70 wt %, based on the total weight of the composition.

3. The composition according to claim 1, wherein the composition has a viscosity of from 0.3 to 200 mPas.

4. A kit for the permanent deformation of hair comprising
   A. an individually packaged composition comprising
      (a) at least one reducing agent comprising a mercapto functional group, and
      (b) at least one alkalizing agent;
   B. an individually packaged malodor suppressant system (c) comprising at least a first malodor suppressant, and a second malodor suppressant, the first and second malodor suppressant form the malodor suppressant system, wherein the first malodor and second malodor suppressants are operanide and isopropyl myristate; and
   C. optionally, an individually packaged fixing composition comprising an oxidizing agent.

5. A method for the permanent deformation of hair comprising the following steps:
   i. providing a permanent shaping composition by mixing
      (a) at least one reducing agent comprising a mercapto functional group,
      (b) at least one alkalizing agent, and
      (c) a malodor suppressant system comprising at least a first malodor suppressant, and a second malodor suppressant and optionally one or more further maloder suppressants, the first and second malodor suppressant and any further maloder suppressant-form the malodor suppressant system, wherein the first malodor and second malodor suppressants each have a molecular weight of from 100 to 400 g/mol, and a distribution coefficient log P (octanol/water) of 2 or more, wherein the first and second malodor suppressant are different compounds;
   ii. applying the permanent shaping composition to the hair before or after putting the hair in a desired shape;
   iii. allowing the permanent shaping composition to act on the hair for a predetermined acting time sufficient for the permanent shaping of the hair;
   iv. rinsing the hair with water;
   v. applying to the hair a fixing composition comprising an oxidizing agent for performing an oxidative post-treatment of the hair; and
   vi. rinsing the hair with water.

* * * * *